United States Patent
Senko

(10) Patent No.: US 7,943,899 B2
(45) Date of Patent: May 17, 2011

(54) METHOD AND APPARATUS FOR IDENTIFYING THE APEX OF A CHROMATOGRAPHIC PEAK

(75) Inventor: Michael W. Senko, Sunnyvale, CA (US)

(73) Assignee: Thermo Finnigan LLC, San Jose, CA (US)

( * ) Notice: Subject to any disclaimer, the term of this patent is extended or adjusted under 35 U.S.C. 154(b) by 802 days.

(21) Appl. No.: 11/644,180

(22) Filed: Dec. 21, 2006

(65) Prior Publication Data

US 2008/0149821 A1  Jun. 26, 2008

(51) Int. Cl.
*H01J 49/26* (2006.01)

(52) U.S. Cl. ............ 250/282; 250/281; 250/292

(58) Field of Classification Search ............ 250/282
See application file for complete search history.

(56) References Cited

U.S. PATENT DOCUMENTS

| | | | | |
|---|---|---|---|---|
| 4,941,101 A * | 7/1990 | Crilly | | 702/32 |
| 4,959,543 A * | 9/1990 | McIver et al. | | 250/291 |
| 5,324,939 A * | 6/1994 | Louris et al. | | 250/292 |
| 5,436,447 A * | 7/1995 | Shew | | 250/291 |
| 5,696,376 A * | 12/1997 | Doroshenko et al. | | 250/292 |
| 5,885,841 A * | 3/1999 | Higgs et al. | | 436/89 |
| 2004/0222369 A1 | 11/2004 | Makarov et al. | | |
| 2004/0251409 A1 | 12/2004 | Le Blanc | | |
| 2005/0261838 A1 | 11/2005 | Andreev et al. | | |
| 2006/0255258 A1 * | 11/2006 | Wang et al. | | 250/282 |
| 2006/0284069 A1 | 12/2006 | Le Blanc | | |
| 2008/0315080 A1 * | 12/2008 | Makarov et al. | | 250/281 |

OTHER PUBLICATIONS

Andreev, et al., "A Universal Denoising and Peak Picking Algorithm for LC-MS Based on Matched Filtration in the Chromatographic Time Domain," Anal. Chem., vol. 75, p. 6314-6326, (2003).

Kohli, et al., "An Alternative Sampling Algorithm for use in Liquid Chromatography/Tandem Mass Spectrometry Experiments," Rapid Comm in Mass Spectrom, vol. 19, p. 589-596, (2005).

Wenner, et al., "Factors that Affect Ion Trap Data-Dependent MS/MS in Proteomics," J Am Soc Mass Spectrom, vol. 15, p. 150-157, (2004).

* cited by examiner

*Primary Examiner* — Phillip A Johnston

(74) *Attorney, Agent, or Firm* — Charles B. Katz; Michael C. Staggs

(57) ABSTRACT

A technique for mass spectrometry includes: receiving first time domain data generated from a chromatographic output, the first time domain data including mass spectra; extracting second time domain data from the first time domain data, the second time domain data corresponding to a selected range of mass-to-charge ratios; transforming the second time domain data into frequency domain data; and identifying, as a function of the frequency domain data, an elution peak for a mass-to-charge ratio within the selected range. Material from the chromatographic output may thereafter be processed as a function of the identified elution peak.

13 Claims, 6 Drawing Sheets

METHOD AND APPARATUS FOR IDENTIFYING THE APEX OF A CHROMATOGRAPHIC PEAK

TECHNICAL FIELD

This invention relates in general to mass spectrometry and, more particularly, to techniques for identifying a chromatographic peak.

BACKGROUND

In mass spectrometry, it is desirable to be able to accurately identify the apex of an elution peak for a particular mass-to-charge ratio. As one typical example, tandem mass spectrometry is a technique that utilizes two or more successive stages of mass analysis with a collision or reaction process occurring between each stage. Two-stage tandem mass spectrometry is typically referred to as mass spectrometry/mass spectrometry (MS/MS). In a data dependent mode, the eluting sample can be automatically selected for further analysis in the second stage when the intensity of a mass spectral peak from the first stage is above a user-specified threshold. Although this type of threshold-based approach has been generally adequate for its intended purposes, it has not been satisfactory in all respects.

For example, a user will often set the threshold at a relatively low value, in order to avoid missing any mass spectral peak that might be of interest. However, this results in masses being selected as soon as they elute and appear above the threshold, or in other words in advance of the occurrence of the apex of the chromatographic peak. As a result, analysis often occurs before the apex of the peak. However, the best spectra can be obtained in the shortest amount of time at the apex of the peak, because the analyte is most concentrated at this point. Unfortunately, it is not a simple matter to identify the apex of a chromatographic peak in real time.

For example, once a peak exceeds a user threshold, the peak could be put on a watch list, and a selection of that peak for second-stage analysis could be delayed while the intensity continues to increase. Then, when the intensity begins to decrease, the peak could be selected. Unfortunately, however, chemical noise and source instability can cause fluctuations in the rising edge of the chromatographic peak. In other words, the rising edge may have an irregularity that causes a temporary decrease, even though the analyte concentration is actually still increasing. To reduce this type of problem, it would be possible to apply smoothing techniques to the data obtained from the first-stage analysis. However, real-time smoothing techniques have a tendency to introduce a phase lag, and the phase lag can create a situation where the smoothed data does not begin decreasing in intensity until after the analyte has completed eluted. In other words, by the time the analyte is selected for further analysis, the chromatographic peak has passed and the analyte is no longer present.

SUMMARY

One of the broader forms of the invention involves a method that includes: receiving first time domain data generated from a chromatographic output, the first time domain data including mass spectra; extracting second time domain data from the first time domain data, the second time domain data corresponding to a selected range of mass-to-charge ratios; transforming the second time domain data into frequency domain data; identifying, as a function of the frequency domain data, an elution peak for a mass-to-charge ratio within the selected range; and processing material from the chromatographic output as a function of the identified elution peak.

Another of the broader forms of the invention involves a computer-readable medium storing a computer program that, when executed: receives first time domain data generated from a chromatographic output, the first time domain data including mass spectra; extracts second time domain data from the first time domain data, the second time domain data corresponding to a selected range of mass-to-charge ratios; transforms the second time domain data into frequency domain data; and identifies, as a function of the frequency domain data, an elution peak for a mass-to-charge ratio within the selected range.

Still another of the broader forms of the invention involves an apparatus having a system that: receives first time domain data generated from a chromatographic output, the first time domain data including mass spectra; extracts second time domain data from the first time domain data, the second time domain data corresponding to a selected range of mass-to-charge ratios; transforms the second time domain data into frequency domain data; and identifies, as a function of the frequency domain data, an elution peak for a mass-to-charge ratio within the selected range.

DETAILED DESCRIPTION

Figure 1:
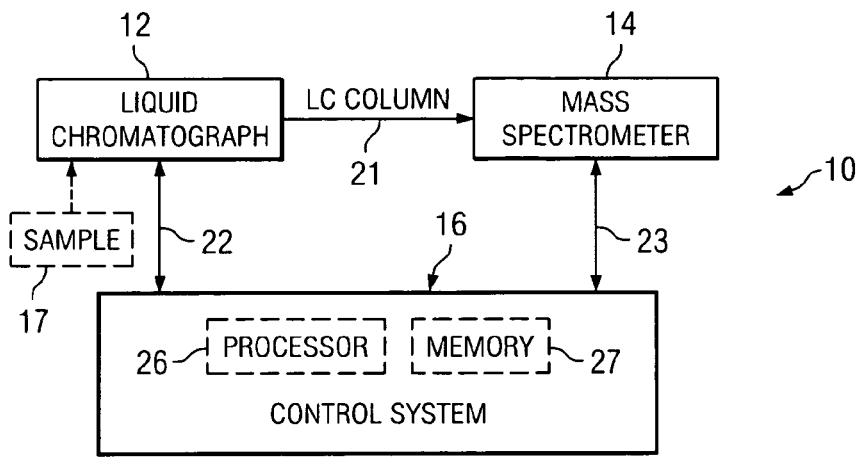
FIG. 1 is a block diagram of an apparatus that embodies aspects of the present invention, including a liquid chromatograph, a mass spectrometer, and a control system.

FIG. 1 is a block diagram of an apparatus 10 that embodies aspects of the present invention. The apparatus 10 includes a liquid chromatograph 12, a mass spectrometer 14, and a control system 16. The liquid chromatograph 12 is a known type of device, and in fact could be any of a number of commercially-available devices. The liquid chromatograph 12 is provided with a sample 17 of a material to be analyzed, and produces particles of that material which are referred to as analytes. In particular, the liquid chromatograph 12 outputs analytes that are atoms or molecules of the sample material 17. The analytes produced by the liquid chromatograph 12 are delivered to the mass spectrometer 14 through a liquid chromatograph (LC) column 21 of a known type. For example, the LC column 21 may be a fused silica capillary tube of a type well-known in the art.

In the disclosed embodiment, the mass spectrometer 14 is a commercially-available device of a known type, for example a device of the type commonly referred to as a triple quadrupole, a q-TOF, an ion trap, an ion trap-FT or an ion trap-Orbitrap. The mass spectrometer 14 is therefore not illustrated and described here in detail. The mass spectrometer 14 is capable of carrying out tandem mass spectrometry. Tandem mass spectrometry involves two or more successive stages of mass analysis, with a collision or reaction process occurring between each stage of mass analysis. The use of two or more successive stages of mass analysis enhances the ability to determine or identify species or compounds of interest from the sample 17. Tandem mass spectrometry that involves two stages of analysis is typically referred to as mass spectrometry/mass spectrometry (MS/MS). In a data dependent approach, analytes from the LC column 21 are processed in the first stage of mass spectrometry, in order to identify mass spectral peaks. When a mass spectral peak is identified, then the analytes associated with the peak are subjected to further evaluation in the second stage of analysis.

The control system 16 is operatively coupled to the liquid chromatograph 12 and the mass spectrometer 14, as indicated diagrammatically at 22 and 23. The disclosed control system 16 includes a processor 26, which may for example be a microprocessor of a known type. The control system also includes a memory 27. In FIG. 1, the memory 27 collectively represents two or more different types of memory. For example, the memory 27 includes a read only memory (ROM) that stores a program executed by the processor 26, as well as static data for the processor 26. In addition, the memory 27 includes some random access memory (RAM) that is used by the processor 26 to store data that changes dynamically during program execution. The processor 26 and the memory 27 could optionally be implemented as respective portions of a known device that is commonly referred to as a microcontroller. Instead of using a processor and associated memory, the circuitry in the control system 16 could alternatively have any other suitable configuration.

As noted above, during tandem mass spectrometry, data from a first stage of mass spectrometry is monitored to identify mass spectral peaks, and the identification of a mass spectral peak then triggers a second stage of mass spectrometry with respect to analytes that correspond to the peak. Pre-existing techniques for identifying a mass spectral peak have been generally adequate for their intended purposes, but have not been entirely satisfactory in all respects. Accordingly, the apparatus 10 of FIG. 1 takes a different approach to the identification of mass spectral peaks. For simplicity and clarity, the discussion that follows will assume that the apparatus 10 is trying to determine whether the sample 17 is a compound having a particular mass-to-charge ratio (m/z) in the mass spectrum.

Figure 2:
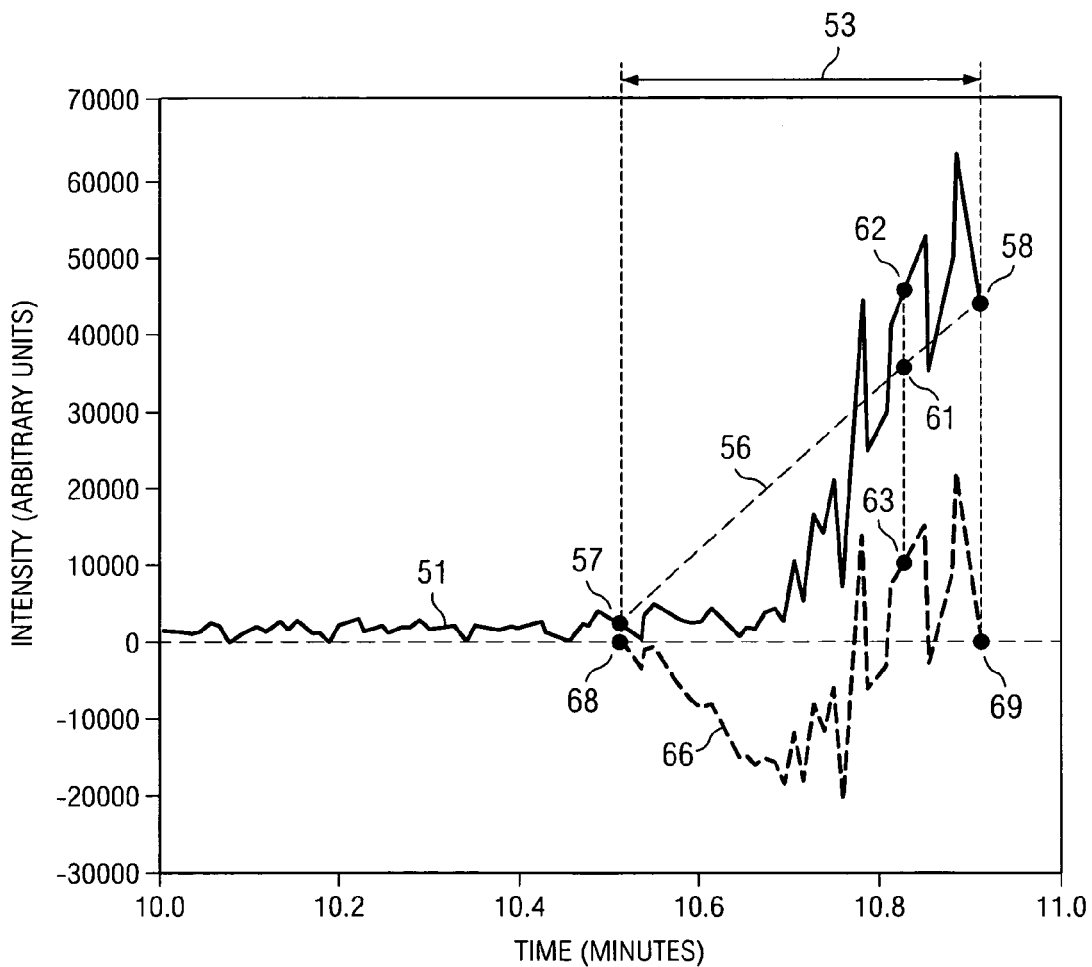
FIG. 2 is a graph showing a curve that is part of an extracted ion chromatogram (XIC) for a selected mass-to-charge ratio, and showing a further curve representing a portion of the XIC curve that has been rotated in preparation for transformation from the time domain to the frequency domain.

Data from the first stage of mass spectrometry is supplied from the mass spectrometer 14 to the control system 16. The control system 16 uses this data to generate an extracted ion chromatogram (XIC) for the particular mass-to-charge ratio of interest. Suitable techniques for generating an XIC are well-known in the art, and are therefore not explained in detail here. FIG. 2 is a graph showing a curve 51 that is part of an XIC for the particular mass-to-charge ratio that is the focus of the present example. In FIG. 2, the horizontal axis represents time in minutes, and the vertical axis represents ion counts, in arbitrary units. According to an aspect of the disclosed technique, a portion of the data from the XIC curve 51 will be converted from the time domain into the frequency domain. In this regard, reference numeral 53 designates a sliding window with a length of approximately 0.4 minutes, or in other words about 24 seconds. The sliding window 53 always ends with the most recently acquired data.

As discussed later, the disclosed embodiment uses a discrete Fourier transform (DFT) to convert data from the time domain to the frequency domain. Alternatively, however, the conversion could be effected using any other suitable transformation technique, including but not limited to a fast Fourier transform, wavelet transform, Hadamard transform, Hilbert transform, or Laplace transform. If the data being converted has starting and ending points with different values, then the transformation can distribute power into the frequency domain spectrum, which is undesirable. Therefore, before effecting a conversion from the time domain to the frequency domain, the data to be transformed is first adjusted or "rotated".

In particular, as shown in FIG. 2, assume that an imaginary line 56 is drawn from the starting point 57 to the ending point 58 of the selected data within the sliding window 53, up to and including the most recently acquired point. Then, within the sliding window 53, the value of each point on the line 56 is subtracted from the corresponding point on the curve 51. For example, the value at point 61 on the line 56 is subtracted from the value at the corresponding point 62 on the XIC curve 51, thereby yielding a value indicated at point 63. This procedure yields rotated data, which is represented in FIG. 2 by the curve 66. It will be noted that the curve 66 has starting and ending points 68 and 69 that have the same value and that are both on the horizontal axis.

Figure 3:
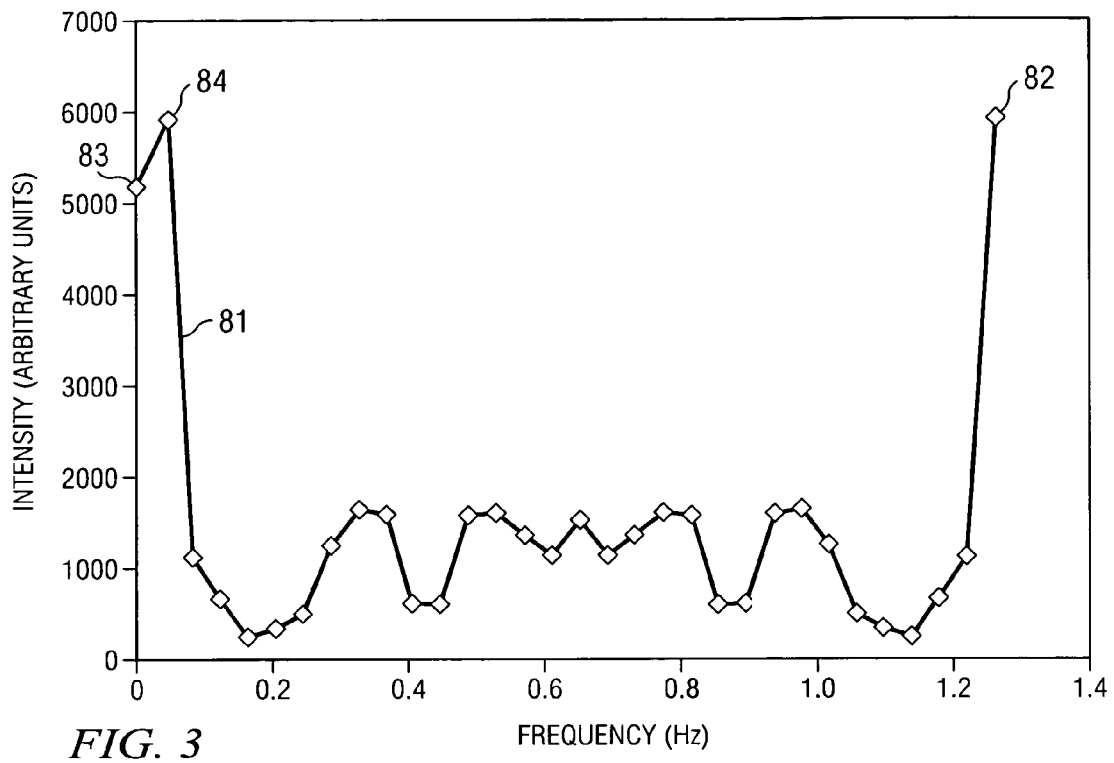
FIG. 3 is a graph showing a curve that represents the magnitude mode frequency domain data obtained by taking the rotated time domain data from FIG. 2 and transforming it into the frequency domain.

Next, the rotated XIC data represented by the curve 66 is transformed from the time domain into the frequency domain using standard DFT processing techniques. FIG. 3 is a graph showing a curve 81 that represents the magnitude mode frequency domain data obtained by taking the time domain data from the curve 66 of FIG. 2 and transforming it into the frequency domain. In the frequency domain, high and low frequency components can be separately identified. In the illustrated example, the source was unstable, as reflected by a relatively large magnitude at 82 for the highest-frequency component. For purposes of the disclosed technique, the component of primary interest is a low-frequency component. The lowest or zero-frequency component, represented by the point 83, is just a measure of the average offset of the data, and can be ignored. The next-lowest component, represented by the point 84, is the "single cycle" frequency. This represents a signal that rotates through one complete cycle over the duration of the transformed time-domain data. This frequency is of primary interest for characterizing and identifying a chromatographic peak.

Figure 4:
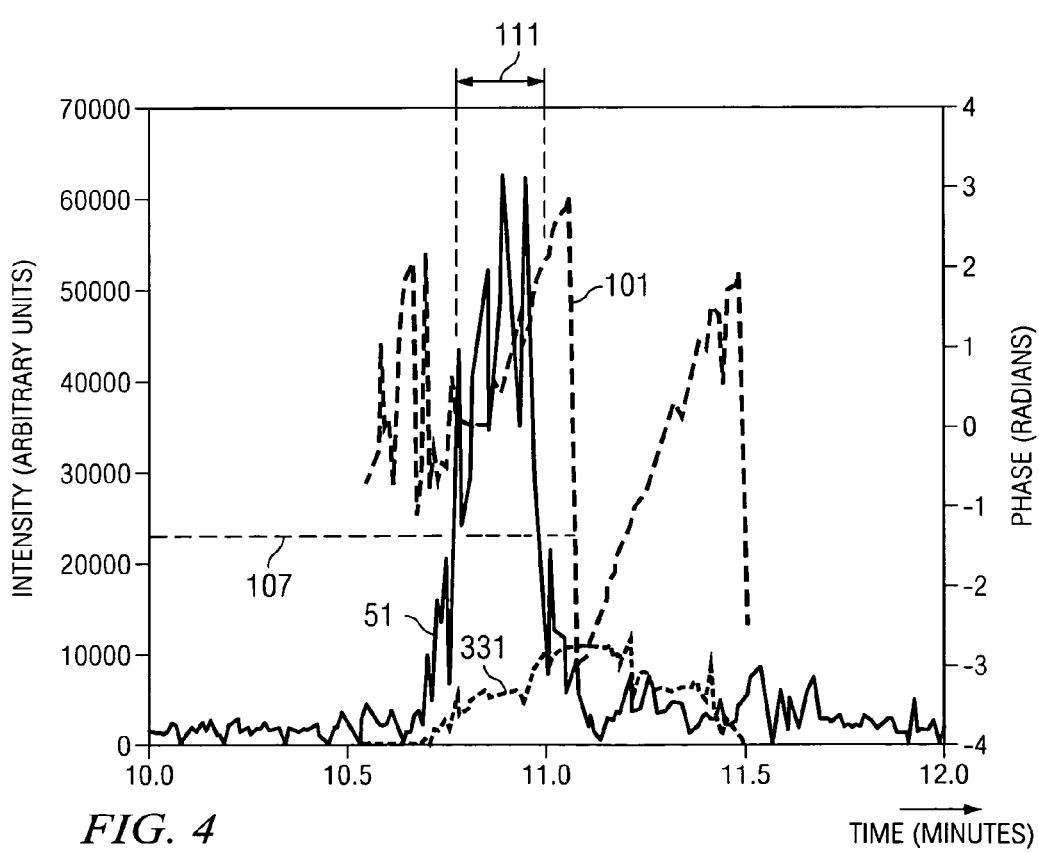
FIG. 4 is a graph showing more of the XIC curve of FIG. 2, showing a further curve representing the magnitude of a single-cycle component of the frequency data in FIG. 3, and showing a phase curve that represents the variation over time of the phase (in radians) of the single-cycle frequency component.

In this regard, the frequency domain data includes information about the phase of the single-cycle frequency. Conceptually, a sine or cosine curve can be fitted to the frequency domain data for the single-cycle frequency. The phase of the single-cycle frequency is the phase of the point on the fitted sine or cosine curve that corresponds to the starting point of the single-cycle frequency data. FIG. 4 is a graph showing the same curve 51 as FIG. 2, except that FIG. 4 shows more of the curve 51. In particular, FIG. 2 shows only the left portion of the curve 51 in FIG. 4. As discussed in association with FIG. 2, the curve 51 is the XIC for the particular mass-to-charge ratio of interest, and represents time-domain data. FIG. 4 depicts a further curve 101 that represents the variation over time of the phase (in radians) of the single-cycle frequency corresponding to the point 84 in FIG. 3. With reference to the vertical axis on the right, it will be noted that, as expected, the phase varies between approximately Π (3.1416) and −Π (−3.1416). Although the curve 51 in FIG. 4 represents time domain data, the curve 101 represents frequency domain data. The curve 51 shows there is a chromatographic peak at a time of approximately 10.9 minutes, and the curve 101 shows that, at this point in time, the phase has a value of approximately Π/2.

With reference to the curve 101, it will be noted that the phase data is very noisy at the start of the peak, or in other words before a time of approximately 10.7 minutes. This is primarily because a low-frequency component is of low magnitude. With significant magnitude, the phase varies smoothly from −Π to Π. At 11.1 minutes, there is an apparent discontinuity in the phase 101, but this is actually the phase wrapping around from Π back down to −Π, rather than a true discontinuity. This phase data can be used to help identify a chromatographic peak. In particular, if the phase has a current value that is within a certain window, for example Π/4 to 3Π/4, then the selected mass-to-charge ratio would be eligible for data dependent selection.

With reference to FIG. 4, it will be noted that there are several different points in time where the phase falls within the window of Π/4 to 3Π/4. Consequently, to accurately identify a chromatographic peak, a further selection criterion is used. In this regard, FIG. 4 shows a user-selected threshold 107. In FIG. 4, the threshold 107 corresponds to an intensity of approximately 23000. However, this is purely by way of example, and a user could select the threshold 107 to be either higher or lower. If the curve 51 is below the threshold, then the phase 101 is ignored. In other words, if the curve 51 is below the threshold 107, then the system does not need to prepare the rotated data 66 (FIG. 2), and does not need to convert this rotated data from the time domain to the frequency domain to obtain phase data. On the other hand, when the curve 51 is above the threshold 107, then the system prepares the rotated data 66 (FIG. 2), converts this rotated data from the time domain to the frequency domain to obtain phase data, and then evaluates the phase data. Thus, in FIG. 4, the portion of the phase data 101 that is actually calculated and taken into account is the portion within a time window 111 when the curve 51 is above the threshold 107. This has the advantage that the processor 26 does not waste time carrying out complex calculations of data that will be ignored.

Figure 5:
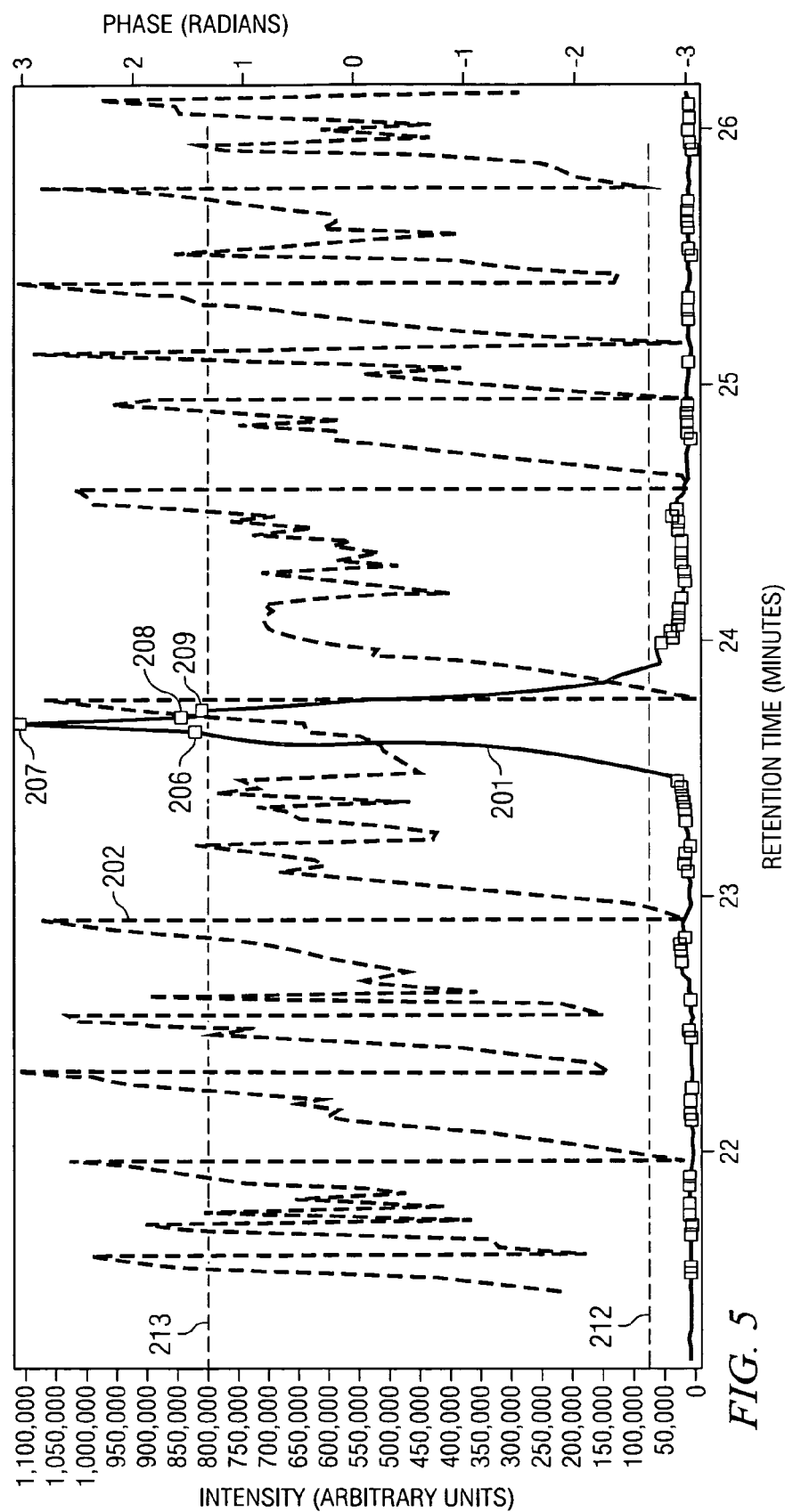
FIGS. 5, 6 and 7 are graphs that are each similar to FIG. 4, and that demonstrate the effect of varying the amount of XIC data transformed from the time domain to the frequency domain.

Proper selection of the length of the sliding time window 53 (FIG. 2) can improve the accuracy with which the foregoing technique identifies an elution peak. In the disclosed embodiment, the sliding window 53 is selected to have a length that is approximately equal to the expected width of the elution peak, as measured at the base of the elution peak. In this regard, FIG. 5 is a graph similar to FIG. 4, in that it shows a time-domain curve 201 that represents an XIC for a selected mass-to-charge ratio, and a frequency-domain curve 202 that represents the phase of the single-cycle frequency. The chromatographic peak in the center of the XIC curve 201 has a base width of approximately 15 seconds, and the phase curve 202 was therefore developed using a sliding window 53 of equal length, or in other words a sliding window with a length of 15 seconds. During the time frame shown in FIG. 5, the mass spectrometer 14 (FIG. 1) carried out a number of scans. During each such scan, the control system 16 (FIG. 1) checks to see whether, at that point in time, the phase value represented by the curve 202 is between 0 and 2 radians. The plurality of points depicted along the curve 201 correspond to the points in time at which a scan occurred while the phase was between 0 and 2 radians. It will be noted that four of these points, identified as 206-209, are all located near the apex of the chromatomatic peak in curve 201.

FIG. 5 also shows a threshold 212 of approximately 75,000, and a further threshold 213 of approximately 800,000. Assume that a user selects a not-illustrated threshold that is anywhere between the two illustrated thresholds 212 and 213, inclusive. In the particular example depicted in FIG. 5, if the phase curve 202 is ignored except when the XIC curve 201 is above that user-selected threshold, only the four points 206-209 will be identified, and any and all of these four points serve to accurately identify the apex of the chromatographic peak.

Figure 6:
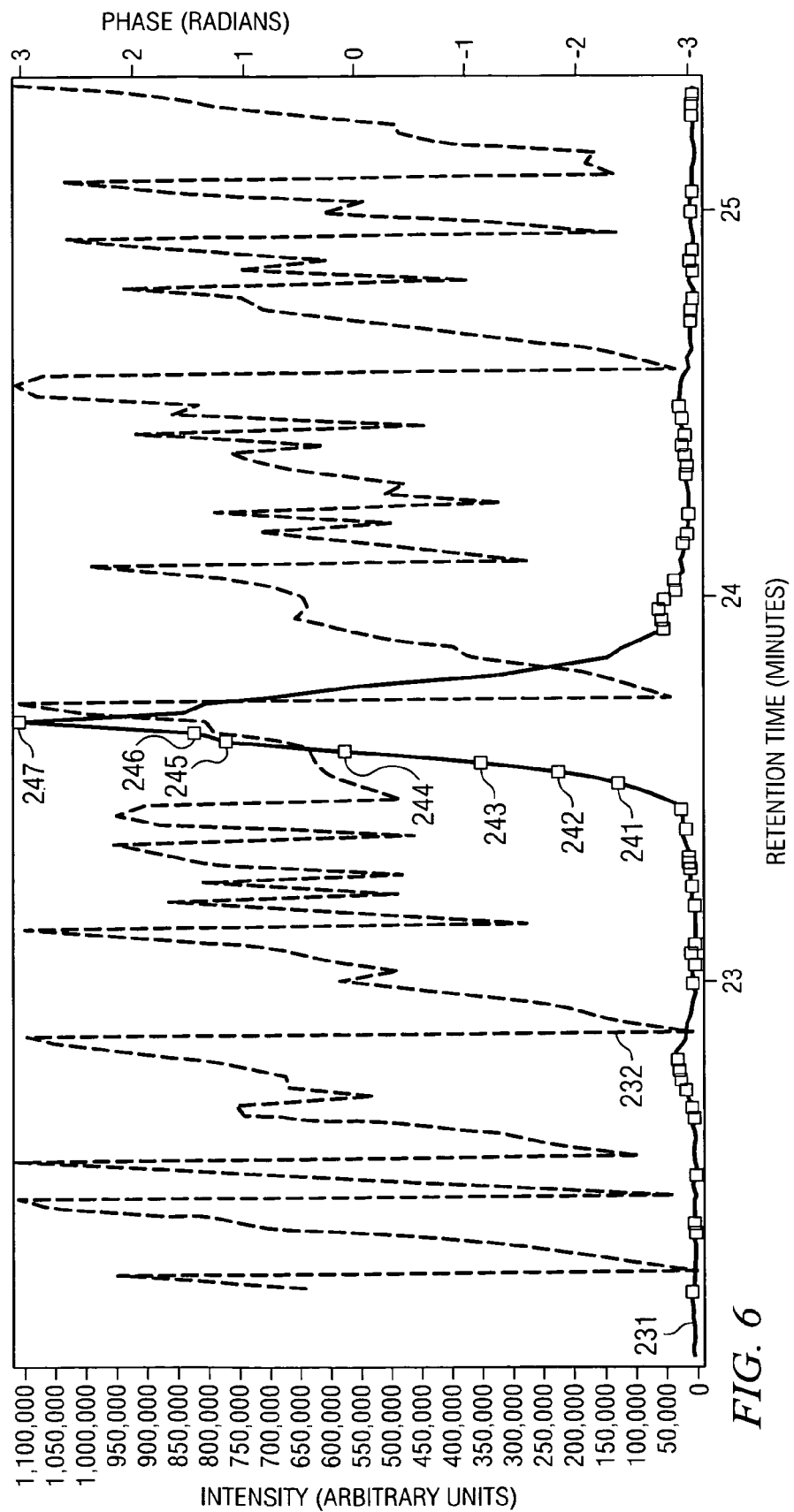

FIG. 6 is a graph similar to FIG. 5, in that it depicts an XIC curve 231, and a corresponding phase curve 232. However, in FIG. 6, the phase curve 232 was generated using a sliding window 53 (FIG. 2) with a length smaller than the base width of the expected chromatographic peak. In particular, in FIG. 6, the chromatographic peak of the curve 231 has a base width of approximately 15 seconds, and the phase curve 232 was generated using a smaller sliding window of approximately 10 seconds. Due to the smaller sliding window, a number of points 241-247 were identified at locations spread out along the rising edge of the chromatographic peak, in contrast to the cluster of points 206-209 located near the apex of the chromatographic peak in FIG. 5.

Figure 7:
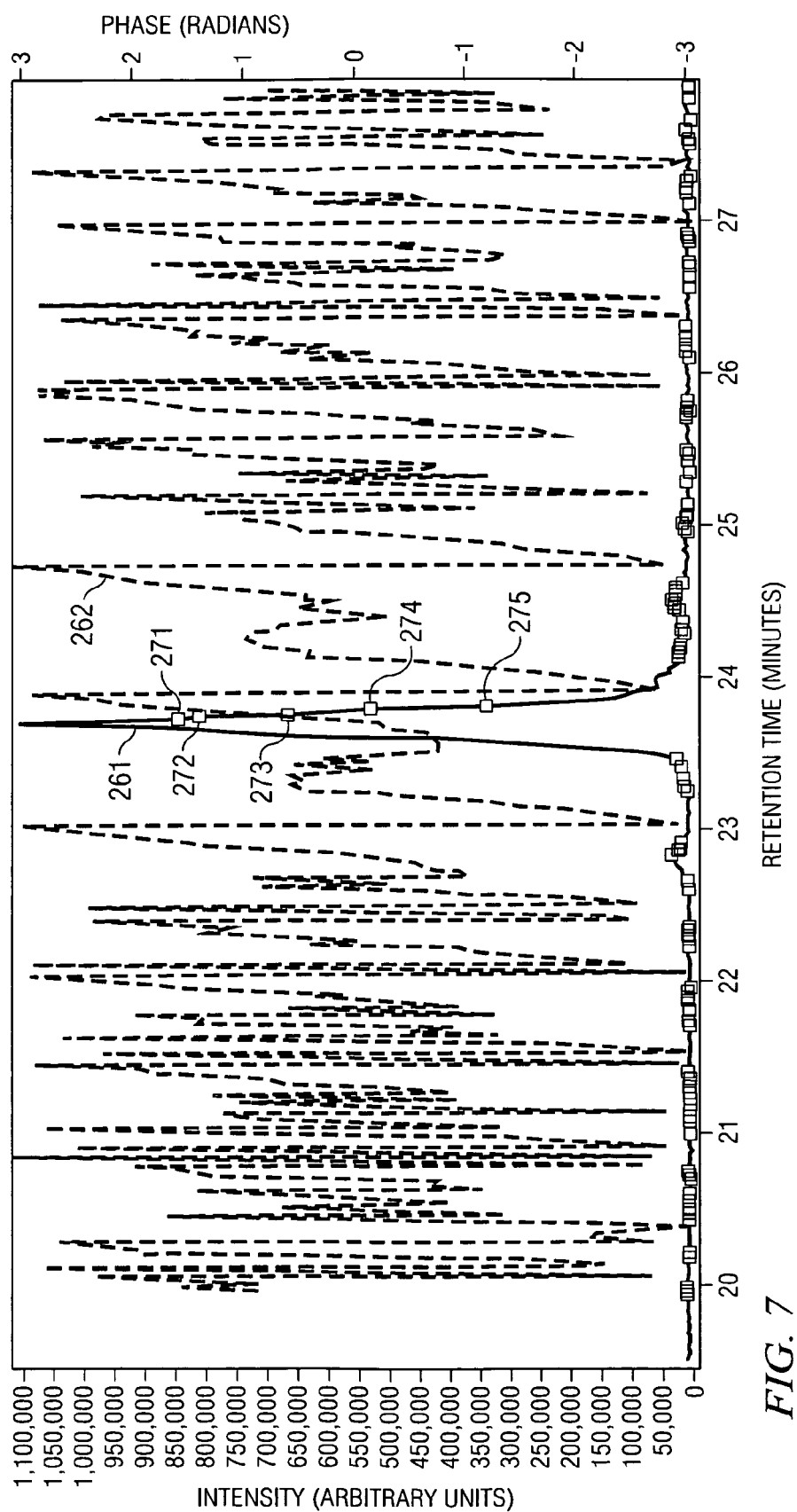

FIG. 7 depicts a further graph similar to FIG. 5, in that it shows an XIC curve 261, and a corresponding phase curve 262. However, in FIG. 7, the phase curve 262 was generated using a sliding window 53 (FIG. 2) with a length larger than the base width of the expected chromatographic peak. In particular, the expected chromatographic peak in FIG. 7 had a base width of approximately 15 seconds, and the sliding window was given a larger width of approximately of 25 seconds. This produced a phase curve in which no points were identified along the rising edge of the chromatographic peak, but several points 271-275 were identified at locations spread out along the falling edge of the chromatographic peak.

Thus, if the sliding window 53 is selected to be smaller than the base width of the expected chromatographic peak, then as shown in FIG. 6, the result will likely be several points 241-247 spread out along the rising edge of the chromatographic peak, rather than a cluster of points 206-209 near the apex of the chromatographic peak, as shown in FIG. 5. Similarly, if the sliding window 53 is selected to be larger than the base width of the expected chromatographic peak, then as shown in FIG. 7, the result will likely be several points 271-275 spread out along the falling edge of the chromatographic peak, rather than a cluster of points 206-209 near the apex of the chromatographic peak, as shown in FIG. 5. FIGS. 5-7 thus demonstrate that it is beneficial to use a sliding window with a width approximately equal to the base width of the expected chromatographic peak, rather than a sliding window that is larger or smaller than the base width of the chromatographic peak. Where the sliding window is given a width that is larger or smaller than the base width of the expected chromatographic peak, the problems discussed above in association with FIGS. 6 and 7 can be ameliorated to some extent by adjusting the phase window. In other words, the phase window would be adjusted to a range different from Π/4 to 3Π/4 radians, or 0 to 2 radians. Even so, it can be beneficial to use a sliding window with a width approximately equal to the base width of the expected chromatographic peak.

Figure 8:
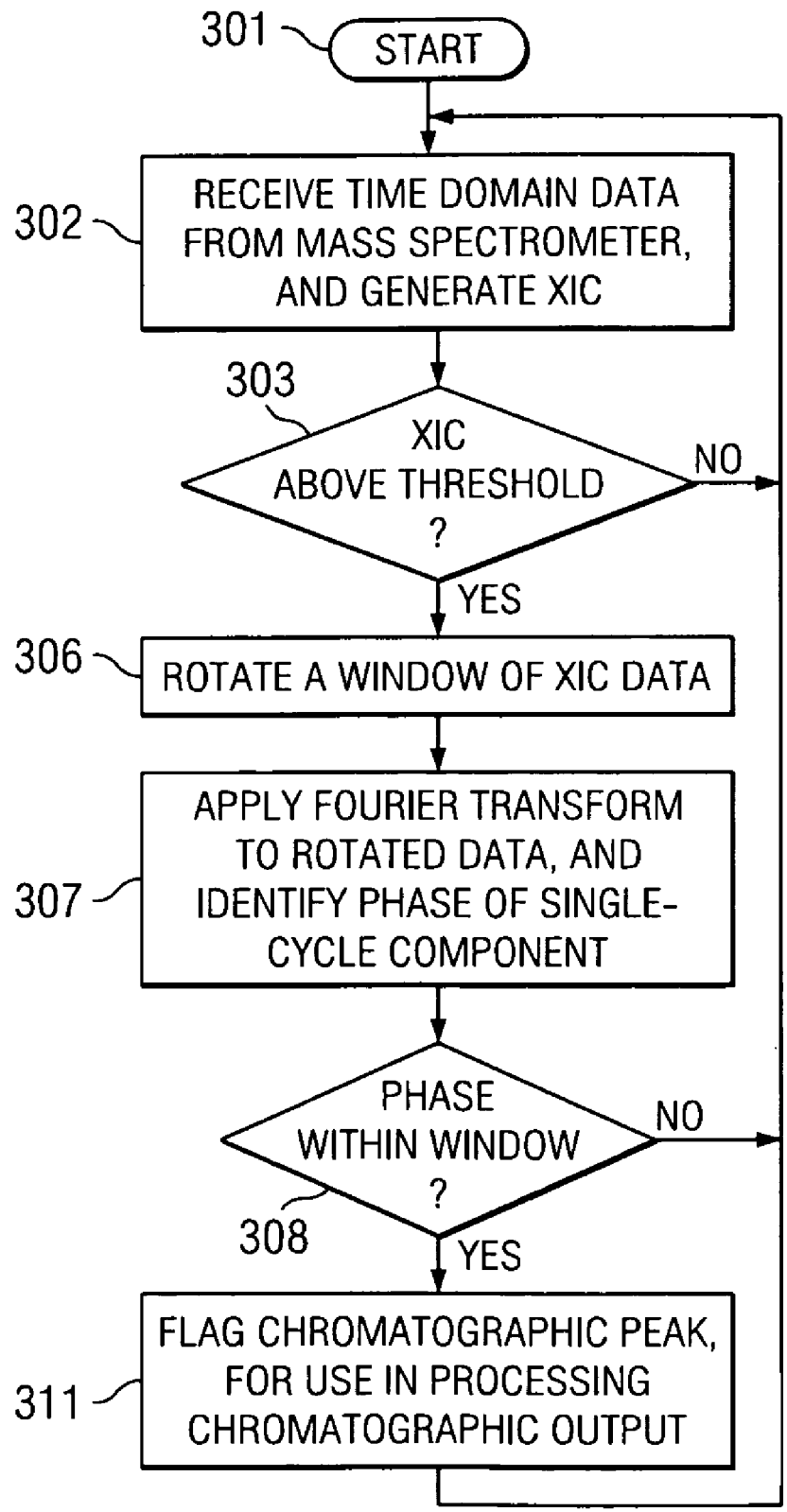
FIG. 8 is a flowchart showing a sequence of operations carried out by a processor in the apparatus of FIG. 1.

FIG. 8 is a flowchart that summarizes the technique described above. In FIG. 8, the processor 26 (FIG. 1) begins in block 301, and proceeds to block 302, where time domain data from the mass spectrometer 14 is used to generate XIC data (such as that depicted at 51 in FIGS. 2 and 4). Control then proceeds to block 303, where a determination is made as to whether the current value of the XIC data is above a threshold, such as the threshold shown at 107 in FIG. 4, or a threshold between the two thresholds 212 and 213 in FIG. 5. If not, then control returns to block 302, in order to continue to receive time domain data and calculate further XIC data for the mass-to-charge ratio of interest, or for a range of mass-to-charge ratios of interest. Thus, in the illustrated example discussed earlier, this would involve calculation of further data for the XIC curve shown at 51 in FIGS. 2 and 4, which corresponds to a particular mass-to-charge ratio of interest.

On the other hand, if it is determined in block 303 that the current XIC data is above the threshold, then control proceeds to block 306, where a window of XIC data is rotated in the manner discussed earlier, in order to obtain rotated data such as that shown at 66 in FIG. 2. Control then proceeds to block 307, where a discrete Fourier transform is used to transform the rotated data from the time domain into the frequency domain, and to then identify the phase of a single-cycle component of the rotated data. In the case of the example discussed above, this would correspond to a point on either the phase curve 101 in FIG. 4.

Control then proceeds to block 308, where a determination is made on whether the current phase value is within a selected window or range, such as Π/4 to 3Π/4 radians, or 0 to 2 radians. If not, then control returns to block 302. Otherwise, control proceeds to block 311, where the system flags the identification of a chromatographic peak, so that this can be subsequently used for processing material of a chromatographic output. For example, the accurate identification of a chromatographic peak can be used to carry out a second mass analysis in tandem mass spectrometry. Alternatively, the accurate identification of a chromatographic peak can be saved, and then used to carry out mass spectrometry in a later scan of the same sample.

In comparison to existing techniques, the technique disclosed herein is superior for identifying the apex of a chromatographic peak, and is superior for eliminating problems caused by source instability. The disclosed technique uses a discrete Fourier transform (DFT). Alternatively, however, the rotated data could be converted from the time domain to the frequency domain using any other suitable type of transform, including a fast Fourier transform (FFT). In the case of a FFT, the FFT will usually expect input data in the form of a number of data points that is a power of two. Since the sliding window 53 (FIG. 2) has a length that is selected based on a time criteria, rather than the amount of data, the number of data points associated with the sliding window will typically not automatically be a power of two. In this case, the time-domain data associated with the sliding window could be supplemented with "dummy" points up to the next power of two, where the dummy points represent a set of values that would maintain continuity between the beginning and end of the rotated data. In the case of an FFT, a further consideration is that the FFT will normally expect data points that are spaced equally in time. The disclosed technique produces data points that may not be spaced equally in time. But in most cases, the unequal spacing of data points should not have a significant effect on the results.

The foregoing discussion is focused on a technique that uses two selection criteria, in particular by determining whether the current value of XIC data is above a threshold, and then determining whether the current value of the phase for a single-cycle frequency is within a selected phase window. However, it is also possible to use other criteria, either in addition to these criteria, or in place of one or both of these two criteria. One such criterion would be to monitor the trend of the phase information, for example by looking for three points in a row where the phase is progressively increasing.

As another alternative, the technique described above contemplates that the real and imaginary components produced by the Fourier transform would be combined. However, it would alternatively be possible to utilize either the real component or the imaginary component, without first combining the two.

Still another alternative selection criterion could be based on the magnitude of the single-cycle frequency component. For example, in FIG. 4, reference numeral 331 designates a curve representing part of the frequency domain data obtained with the Fourier transform. More specifically, the curve 331 represents the variation over time of the magnitude of the single-cycle component in the frequency domain. Instead of comparing the XIC curve 51 to the threshold 107 in order to determine whether or not to consider phase data, the magnitude of the curve 331 could be compared to an appropriate threshold in order to determine whether or not to consider phase data.

Still another alternative selection criterion would involve use of the rotation angle of the rotated data. For example, with reference to FIG. 2, if the portion of the XIC curve 51 that is to be rotated has a starting point 57 with a value lower than the value of the end point 58, then rotation followed by Fourier transformation would be carried out. In contrast, if the starting point 57 had a value higher than the value of the end point 58, then rotation and Fourier transformation would not be carried out. This rotation angle criterion could, for example, be used in combination with the above-mentioned phase criterion, and the above-mentioned threshold criterion for the curve 331 in FIG. 4.

Further, as discussed above in association with FIG. 2, the XIC curve 51 is generated using known techniques. These known techniques typically involve "binning" of mass-to-charge ratios detected by the mass spectrometer. For the purpose of the technique described in association with FIGS. 1-8, binning would typically be done at unit resolution, or in other words with bin widths of 1 m/z per bin. However, it would alternatively be possible to use wider bins, and the disclosed technique would still be effective in spotting eluting peaks. Of course, with wider bins the frequency data obtained using the Fourier transform would be slightly noisier. But where this noise could be tolerated, then initial binning could occur using a wider width such as 5 m/z per bin. Then, any of the wider bins that met all selection criteria could be further analyzed at a higher binning resolution such as 1 m/z per bin, in order to more accurately identify a mass of interest. For instruments with high resolution capabilities, such as FTICR and orbitrap, narrower bins could be used to assist in separating distinct masses. A further factor that could influence bin width is the particular type of sample material 17 (FIG. 1) that is being analyzed. For example, samples with more complex mixtures might require finer binning than relatively simple samples.

Although different selected embodiments have been illustrated and described in detail, it will be understood that they are exemplary, and that a variety of substitutions and alterations are possible without departing from the spirit and scope of the present invention, as defined by the following claims.

What is claimed is:

1. An analytical method comprising:
supplying a sample to a liquid chromatography column, and directing the output of the column to a mass spectrometer;
generating at the mass spectrometer first time domain data, the first time domain data including mass spectra representative of the mass-to-charge ratios and abundances of ions produced from the sample;

extracting second time domain data from the first time domain data, the second time domain data corresponding to the abundances of ions having a selected range of mass-to-charge ratios;

transforming the second time domain data into frequency domain data;

determining a phase of a single-cycle component in the frequency domain data; and triggering a data-dependent action if the determined phase meets a specified criterion.

2. A method according to claim 1, wherein the step of transforming is performed only when a current value of the second time domain data is above a specified threshold.

3. A method according to claim 1, wherein the step of transforming includes applying a discrete Fourier transform (DFT) to the second time domain data.

4. A method according to claim 1, wherein the step of transforming the second time domain data is performed only for data acquired during a sliding time window.

5. A method according to claim 4, wherein the width of the sliding window is selected to correspond to the expected width of the elution peak.

6. A method according to claim 4, wherein the step of transforming includes rotating the second time domain data so that starting and ending points thereof have approximately the same value.

7. A method according to claim 1, wherein the data-dependent action includes performing tandem mass spectrometry.

8. The method of claim 1, wherein the step of performing a data-dependent action includes determining whether the phase is between $\pi/4$ and $3\pi/4$ radians.

9. The method of claim 1, wherein the step of performing a data-dependent action includes determining whether the phase is between 0 and 2 radians.

10. The method of claim 1, wherein the step of determining a phase is performed only if the magnitude of the single-cycle component exceeds a specified threshold.

11. The method of claim 6, wherein the second time domain data is transformed into frequency domain data only if a rotation angle of the rotated second time domain data meets a specified rotation angle criterion.

12. The method of claim 1, wherein the step of performing a data-dependent action includes monitoring a trend of the phase over time.

13. A mass spectrometer, comprising:

a mass analyzer for receiving an analyte sample from a liquid chromatography column, the mass analyzer producing signals representing first time domain data including mass spectra representative of the mass-to-charge ratios and abundances of ions produced from the sample; and a control system, coupled to the mass analyzer, programmed with instructions for extracting second time domain data from the first time domain data, the second time domain data corresponding to the abundances of ions having a selected range of mass-to-charge ratios, transforming the second time domain data into frequency domain data, determining a phase of a single-cycle component in the frequency domain data, and triggering a data-dependent action if the determined phase meets a specified criterion.

* * * * *